United States Patent
Foster et al.

(10) Patent No.: US 9,050,457 B2
(45) Date of Patent: *Jun. 9, 2015

(54) MRI CONDITIONALLY SAFE LEAD WITH LOW-PROFILE CONDUCTOR FOR LONGITUDINAL EXPANSION

(71) Applicant: Cardiac Pacemakers, Inc., St. Paul, MN (US)

(72) Inventors: Arthur J. Foster, Blaine, MN (US); Christopher R. Perrey, Victoria, MN (US); Stephen E. DeRoche, St. Paul, MN (US); Timothy R. Jackson, Minneapolis, MN (US); Andrew L. De Kock, Andover, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/174,358

(22) Filed: Feb. 6, 2014

(65) Prior Publication Data

US 2014/0155972 A1 Jun. 5, 2014

Related U.S. Application Data

(63) Continuation of application No. 13/767,445, filed on Feb. 14, 2013, now Pat. No. 8,676,351, which is a continuation of application No. 12/940,489, filed on Nov. 5, 2010, now Pat. No. 8,391,994.

(60) Provisional application No. 61/291,556, filed on Dec. 31, 2009.

(51) Int. Cl.
*A61N 1/05* (2006.01)
*A61N 1/08* (2006.01)
(Continued)

(52) U.S. Cl.
CPC ........ *A61N 1/08* (2013.01); *A61N 1/056* (2013.01); *A61N 1/3718* (2013.01); *A61N 1/3925* (2013.01); *A61N 2001/086* (2013.01); *A61N 1/05* (2013.01)

(58) Field of Classification Search
USPC .......................................... 607/119
See application file for complete search history.

(56) References Cited

U.S. PATENT DOCUMENTS

| 3,614,692 A | 10/1971 | Rozelle et al. |
|---|---|---|
| 4,131,759 A | 12/1978 | Felkel |

(Continued)

FOREIGN PATENT DOCUMENTS

| CN | 1762510 A | 4/2006 |
|---|---|---|
| CN | 1905789 A | 1/2007 |

(Continued)

OTHER PUBLICATIONS

Third Party Submission Under 37 CFR 1.290 filed in U.S. Appl. No. 14/056,746 on May 20, 2014, 13 pages.

(Continued)

*Primary Examiner* — Carl H Layno
*Assistant Examiner* — Jon Eric C Morales
(74) *Attorney, Agent, or Firm* — Faegre Baker Daniels LLP

(57) ABSTRACT

An implantable electrical lead includes a lead body and a multi-layer coil conductor extending within the lead body. The multi-layer coil conductor includes a first coil layer and a second coil layer disposed about the first coil layer. The first and second coil layers are configured such that the multi-layer coil conductor has an axial stiffness substantially equal to an axial stiffness of the lead body adjacent to the multi-layer coil conductor.

20 Claims, 5 Drawing Sheets

(51) Int. Cl.
   *A61N 1/37*  (2006.01)
   *A61N 1/39*  (2006.01)

(56) References Cited

U.S. PATENT DOCUMENTS

| | | |
|---|---|---|
| 4,135,518 A | 1/1979 | Dutcher |
| 4,146,036 A | 3/1979 | Benjamin et al. |
| 4,209,019 A | 6/1980 | Dutcher et al. |
| 4,253,462 A | 3/1981 | Dutcher et al. |
| 4,350,169 A | 9/1982 | Dutcher et al. |
| 4,381,013 A | 4/1983 | Dutcher |
| 4,404,125 A | 9/1983 | Abolins et al. |
| 4,437,474 A | 3/1984 | Peers-Trevarton |
| 4,484,586 A | 11/1984 | McMickle et al. |
| 4,493,329 A | 1/1985 | Crawford et al. |
| 4,574,800 A | 3/1986 | Peers-Trevarton |
| 4,643,202 A | 2/1987 | Roche |
| 4,649,938 A | 3/1987 | McArthur |
| 4,869,970 A | 9/1989 | Gulla et al. |
| 5,002,067 A | 3/1991 | Berthelsen et al. |
| 5,003,975 A | 4/1991 | Hafelfinger et al. |
| 5,020,545 A | 6/1991 | Soukup |
| 5,056,516 A | 10/1991 | Spehr |
| 5,074,313 A | 12/1991 | Dahl et al. |
| 5,144,960 A | 9/1992 | Mehra et al. |
| 5,201,865 A | 4/1993 | Kuehn |
| 5,217,010 A | 6/1993 | Tsitlik et al. |
| 5,222,506 A | 6/1993 | Patrick et al. |
| 5,231,996 A | 8/1993 | Bardy et al. |
| 5,241,957 A | 9/1993 | Camps et al. |
| 5,243,911 A | 9/1993 | Dow et al. |
| 5,246,014 A | 9/1993 | Williams et al. |
| 5,259,395 A | 11/1993 | Li |
| 5,300,108 A | 4/1994 | Rebell et al. |
| 5,324,322 A | 6/1994 | Grill, Jr. et al. |
| 5,330,522 A | 7/1994 | Kreyenhagen |
| 5,354,327 A | 10/1994 | Smits |
| 5,370,666 A | 12/1994 | Lindberg et al. |
| 5,378,234 A | 1/1995 | Hammerslag et al. |
| 5,387,199 A | 2/1995 | Siman et al. |
| 5,417,208 A | 5/1995 | Winkler |
| 5,425,755 A | 6/1995 | Doan |
| 5,456,707 A | 10/1995 | Giele |
| 5,476,485 A | 12/1995 | Weinberg et al. |
| 5,483,022 A | 1/1996 | Mar |
| 5,522,872 A | 6/1996 | Hoff |
| 5,522,875 A | 6/1996 | Gates et al. |
| 5,534,018 A | 7/1996 | Wahlstrand et al. |
| 5,542,173 A | 8/1996 | Mar et al. |
| 5,545,205 A | 8/1996 | Schulte et al. |
| 5,549,646 A | 8/1996 | Katz et al. |
| 5,554,139 A | 9/1996 | Okajima |
| 5,574,249 A | 11/1996 | Lindsay |
| 5,584,873 A | 12/1996 | Shoberg et al. |
| 5,599,576 A | 2/1997 | Opolski |
| 5,609,622 A | 3/1997 | Soukup et al. |
| 5,618,208 A | 4/1997 | Crouse et al. |
| 5,727,552 A | 3/1998 | Ryan |
| 5,727,553 A | 3/1998 | Saad |
| 5,728,149 A | 3/1998 | Laske et al. |
| 5,755,742 A | 5/1998 | Schuelke et al. |
| 5,760,341 A | 6/1998 | Laske et al. |
| 5,766,227 A | 6/1998 | Nappholz et al. |
| 5,800,496 A | 9/1998 | Swoyer et al. |
| 5,810,887 A | 9/1998 | Accorti, Jr. et al. |
| 5,817,136 A | 10/1998 | Nappholz et al. |
| 5,824,026 A | 10/1998 | Diaz |
| 5,833,715 A | 11/1998 | Vachon et al. |
| 5,849,031 A | 12/1998 | Martinez et al. |
| 5,891,114 A | 4/1999 | Chien et al. |
| 5,891,179 A | 4/1999 | Er et al. |
| 5,935,159 A | 8/1999 | Cross, Jr. et al. |
| 5,957,966 A | 9/1999 | Schroeppel et al. |
| 5,957,970 A | 9/1999 | Shoberg et al. |
| 5,968,087 A | 10/1999 | Hess et al. |
| 6,016,447 A | 1/2000 | Juran et al. |
| 6,057,031 A | 5/2000 | Breme et al. |
| 6,078,840 A | 6/2000 | Stokes |
| 6,083,216 A | 7/2000 | Fischer, Sr. |
| 6,101,417 A | 8/2000 | Vogel et al. |
| 6,106,522 A | 8/2000 | Fleischman et al. |
| 6,141,593 A | 10/2000 | Patag |
| 6,143,013 A | 11/2000 | Samson et al. |
| 6,178,355 B1 | 1/2001 | Williams et al. |
| 6,192,280 B1 | 2/2001 | Sommer et al. |
| 6,208,881 B1 | 3/2001 | Champeau |
| 6,249,708 B1 | 6/2001 | Nelson et al. |
| 6,256,541 B1 | 7/2001 | Heil et al. |
| 6,259,954 B1 | 7/2001 | Conger et al. |
| 6,289,250 B1 | 9/2001 | Tsuboi et al. |
| 6,295,476 B1 | 9/2001 | Schaenzer |
| 6,304,784 B1 | 10/2001 | Allee et al. |
| 6,317,633 B1 | 11/2001 | Jorgenson et al. |
| 6,360,129 B1 | 3/2002 | Ley et al. |
| 6,400,992 B1 | 6/2002 | Borgersen et al. |
| 6,428,537 B1 | 8/2002 | Swanson et al. |
| 6,434,430 B2 | 8/2002 | Borgersen et al. |
| 6,456,888 B1 | 9/2002 | Skinner et al. |
| 6,493,591 B1 | 12/2002 | Stokes |
| 6,501,991 B1 | 12/2002 | Honeck et al. |
| 6,501,994 B1 | 12/2002 | Janke et al. |
| 6,510,345 B1 | 1/2003 | Van Bentem |
| 6,516,230 B2 | 2/2003 | Williams et al. |
| 6,526,321 B1 | 2/2003 | Spehr |
| 6,564,107 B1 | 5/2003 | Bodner et al. |
| 6,671,554 B2 | 12/2003 | Gibson et al. |
| 6,701,191 B2 | 3/2004 | Schell |
| 6,721,600 B2 | 4/2004 | Jorgenson et al. |
| 6,721,604 B1 | 4/2004 | Robinson et al. |
| 6,813,521 B2 | 11/2004 | Bischoff et al. |
| 6,850,803 B1 | 2/2005 | Jimenez et al. |
| 6,854,994 B2 | 2/2005 | Stein et al. |
| 6,866,044 B2 | 3/2005 | Bardy et al. |
| 6,906,256 B1 | 6/2005 | Wang |
| 6,920,361 B2 | 7/2005 | Williams |
| 6,925,334 B1 | 8/2005 | Salys |
| 6,944,489 B2 | 9/2005 | Zeijlemaker et al. |
| 6,949,929 B2 | 9/2005 | Gray et al. |
| 6,978,185 B2 | 12/2005 | Osypka |
| 6,985,755 B2 | 1/2006 | Cadieux et al. |
| 6,985,775 B2 | 1/2006 | Reinke et al. |
| 6,993,373 B2 | 1/2006 | Vrijheid et al. |
| 6,999,818 B2 | 2/2006 | Stevenson et al. |
| 6,999,821 B2 | 2/2006 | Jenney et al. |
| 7,013,180 B2 | 3/2006 | Dublin et al. |
| 7,013,182 B1 | 3/2006 | Krishnan |
| 7,047,075 B2 | 5/2006 | Stubbs |
| 7,047,083 B2 | 5/2006 | Gunderson et al. |
| 7,050,855 B2 | 5/2006 | Zeijlemaker et al. |
| 7,113,827 B2 | 9/2006 | Silvestri et al. |
| 7,123,013 B2 | 10/2006 | Gray |
| 7,127,294 B1 | 10/2006 | Wang et al. |
| 7,135,978 B2 | 11/2006 | Gisselberg et al. |
| 7,138,582 B2 | 11/2006 | Lessar et al. |
| 7,158,837 B2 | 1/2007 | Osypka et al. |
| 7,174,219 B2 | 2/2007 | Wahlstrand et al. |
| 7,174,220 B1 | 2/2007 | Chitre et al. |
| 7,205,768 B2 | 4/2007 | Schulz et al. |
| 7,239,916 B2 | 7/2007 | Thompson et al. |
| 7,242,987 B2 | 7/2007 | Holleman et al. |
| 7,257,449 B2 | 8/2007 | Bodner |
| 7,289,851 B2 | 10/2007 | Gunderson et al. |
| 7,363,090 B2 | 4/2008 | Halperin et al. |
| 7,369,898 B1 | 5/2008 | Kroll et al. |
| 7,378,931 B2 | 5/2008 | Odahara et al. |
| 7,388,378 B2 | 6/2008 | Gray et al. |
| 7,389,148 B1 | 6/2008 | Morgan |
| 7,453,344 B2 | 11/2008 | Maeda et al. |
| 7,535,363 B2 | 5/2009 | Gisselberg et al. |
| 7,571,010 B2 | 8/2009 | Zarembo et al. |
| 7,610,101 B2 | 10/2009 | Wedan et al. |
| 7,630,761 B2 | 12/2009 | Salo et al. |
| 7,689,291 B2 | 3/2010 | Polkinghorne et al. |
| 7,765,005 B2 | 7/2010 | Stevenson |

(56) References Cited

U.S. PATENT DOCUMENTS

| | | |
|---|---|---|
| 7,853,332 B2 | 12/2010 | Olsen et al. |
| 7,877,150 B2 | 1/2011 | Hoegh et al. |
| 7,912,552 B2 | 3/2011 | Przybyszewski |
| 7,917,213 B2 | 3/2011 | Bulkes et al. |
| 7,933,662 B2 | 4/2011 | Marshall et al. |
| 7,953,499 B2 | 5/2011 | Knapp et al. |
| 7,986,999 B2 | 7/2011 | Wedan et al. |
| 7,991,484 B1 | 8/2011 | Sengupta et al. |
| 8,000,801 B2 | 8/2011 | Stevenson et al. |
| 8,027,736 B2 | 9/2011 | Wahlstrand et al. |
| 8,032,230 B1 | 10/2011 | Cox et al. |
| 8,046,084 B2 | 10/2011 | Bodner |
| 8,099,177 B2 | 1/2012 | Dahlberg |
| 8,103,360 B2 | 1/2012 | Foster |
| 8,108,054 B2 | 1/2012 | Helland |
| 8,145,324 B1 | 3/2012 | Stevenson et al. |
| 8,170,688 B2 | 5/2012 | Wedan et al. |
| 8,200,342 B2 | 6/2012 | Stevenson et al. |
| 8,214,055 B2 | 7/2012 | Erickson |
| 8,244,346 B2 | 8/2012 | Foster et al. |
| 8,255,055 B2 | 8/2012 | Ameri |
| 8,306,630 B2 | 11/2012 | Stubbs et al. |
| 8,315,715 B2 | 11/2012 | Erickson |
| 8,332,050 B2 | 12/2012 | Perrey et al. |
| 8,335,572 B2 | 12/2012 | Ameri |
| 8,391,994 B2 * | 3/2013 | Foster et al. .............. 607/119 |
| 8,401,671 B2 | 3/2013 | Wedan et al. |
| 8,543,209 B2 | 9/2013 | Tyers et al. |
| 8,543,218 B2 | 9/2013 | Erickson |
| 8,666,508 B2 | 3/2014 | Foster et al. |
| 8,666,512 B2 | 3/2014 | Walker et al. |
| 8,670,828 B2 | 3/2014 | Hall et al. |
| 8,670,840 B2 | 3/2014 | Wedan et al. |
| 8,676,344 B2 | 3/2014 | Desai et al. |
| 8,676,351 B2 | 3/2014 | Foster et al. |
| 8,682,451 B2 | 3/2014 | Wengreen et al. |
| 8,688,236 B2 | 4/2014 | Foster |
| 8,731,685 B2 | 5/2014 | Ameri |
| 8,744,600 B2 | 6/2014 | Perrey et al. |
| 8,798,767 B2 | 8/2014 | Foster et al. |
| 8,825,179 B2 | 9/2014 | Walker et al. |
| 8,825,181 B2 | 9/2014 | Foster et al. |
| 2002/0065544 A1 | 5/2002 | Smits |
| 2002/0072769 A1 | 6/2002 | Silvian et al. |
| 2002/0111664 A1 | 8/2002 | Bartig et al. |
| 2002/0128689 A1 | 9/2002 | Connelly et al. |
| 2002/0144720 A1 | 10/2002 | Zahorik et al. |
| 2003/0028231 A1 | 2/2003 | Partridge et al. |
| 2003/0050680 A1 | 3/2003 | Gibson et al. |
| 2003/0083723 A1 | 5/2003 | Wilkinson et al. |
| 2003/0083726 A1 | 5/2003 | Zeijlemaker et al. |
| 2003/0092303 A1 | 5/2003 | Osypka |
| 2003/0093136 A1 | 5/2003 | Osypka et al. |
| 2003/0093138 A1 | 5/2003 | Osypka et al. |
| 2003/0139794 A1 | 7/2003 | Jenney et al. |
| 2003/0140931 A1 | 7/2003 | Zeijlemaker et al. |
| 2003/0144705 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0014355 A1 | 1/2004 | Osypka et al. |
| 2004/0064161 A1 | 4/2004 | Gunderson et al. |
| 2004/0064173 A1 | 4/2004 | Hine et al. |
| 2004/0064174 A1 | 4/2004 | Belden |
| 2004/0088033 A1 | 5/2004 | Smits et al. |
| 2004/0097965 A1 | 5/2004 | Gardeski et al. |
| 2004/0122490 A1 | 6/2004 | Reinke et al. |
| 2004/0153049 A1 | 8/2004 | Hewitt et al. |
| 2004/0162600 A1 | 8/2004 | Williams |
| 2004/0167442 A1 | 8/2004 | Shireman et al. |
| 2004/0172117 A1 | 9/2004 | Hill et al. |
| 2004/0193140 A1 | 9/2004 | Griffin et al. |
| 2004/0243210 A1 | 12/2004 | Morgan et al. |
| 2004/0267107 A1 | 12/2004 | Lessar et al. |
| 2005/0070972 A1 | 3/2005 | Wahlstrand et al. |
| 2005/0090886 A1 | 4/2005 | MacDonald et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0136385 A1 | 6/2005 | Mann et al. |
| 2005/0177135 A1 | 8/2005 | Hildebrand et al. |
| 2005/0182471 A1 | 8/2005 | Wang |
| 2005/0197677 A1 | 9/2005 | Stevenson |
| 2005/0222642 A1 | 10/2005 | Przybyszewski et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0246007 A1 | 11/2005 | Sommer et al. |
| 2005/0267556 A1 | 12/2005 | Shuros et al. |
| 2005/0272280 A1 | 12/2005 | Osypka |
| 2005/0283167 A1 | 12/2005 | Gray |
| 2006/0009819 A1 | 1/2006 | Przybyszewski |
| 2006/0030774 A1 | 2/2006 | Gray et al. |
| 2006/0037461 A1 | 2/2006 | Yasumura |
| 2006/0041293 A1 | 2/2006 | Mehdizadeh et al. |
| 2006/0041294 A1 | 2/2006 | Gray |
| 2006/0041296 A1 | 2/2006 | Bauer et al. |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0106442 A1 | 5/2006 | Richardson et al. |
| 2006/0118758 A1 | 6/2006 | Wang et al. |
| 2006/0129043 A1 | 6/2006 | Ben-Jacob et al. |
| 2006/0167536 A1 | 7/2006 | Nygren et al. |
| 2006/0200218 A1 | 9/2006 | Wahlstrand |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0253180 A1 | 11/2006 | Zarembo et al. |
| 2006/0271138 A1 | 11/2006 | MacDonald |
| 2006/0293737 A1 | 12/2006 | Krishnan |
| 2007/0010702 A1 | 1/2007 | Wang et al. |
| 2007/0027532 A1 | 2/2007 | Wang et al. |
| 2007/0106332 A1 | 5/2007 | Denker et al. |
| 2007/0112398 A1 | 5/2007 | Stevenson et al. |
| 2007/0156205 A1 | 7/2007 | Larson et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0208383 A1 | 9/2007 | Williams |
| 2007/0255378 A1 | 11/2007 | Polkinghorne et al. |
| 2008/0009905 A1 | 1/2008 | Zeijlemaker |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0051854 A1 | 2/2008 | Bulkes et al. |
| 2008/0057784 A1 | 3/2008 | Zarembo et al. |
| 2008/0058902 A1 | 3/2008 | Gray et al. |
| 2008/0119917 A1 | 5/2008 | Geistert |
| 2008/0125754 A1 | 5/2008 | Beer et al. |
| 2008/0129435 A1 | 6/2008 | Gray |
| 2008/0132985 A1 | 6/2008 | Wedan et al. |
| 2008/0132986 A1 | 6/2008 | Gray et al. |
| 2008/0140152 A1 | 6/2008 | Imran et al. |
| 2008/0154348 A1 | 6/2008 | Atalar et al. |
| 2008/0208290 A1 | 8/2008 | Phillips et al. |
| 2008/0243218 A1 | 10/2008 | Bottomley et al. |
| 2008/0262584 A1 | 10/2008 | Bottomley et al. |
| 2008/0269831 A1 | 10/2008 | Erickson |
| 2009/0005825 A1 | 1/2009 | MacDonald |
| 2009/0024180 A1 | 1/2009 | Kisker et al. |
| 2009/0024197 A1 | 1/2009 | Jensen |
| 2009/0099440 A1 | 4/2009 | Viohl |
| 2009/0099555 A1 | 4/2009 | Viohl et al. |
| 2009/0118610 A1 | 5/2009 | Karmarkar et al. |
| 2009/0149920 A1 | 6/2009 | Li et al. |
| 2009/0149933 A1 | 6/2009 | Ameri |
| 2009/0149934 A1 | 6/2009 | Ameri et al. |
| 2009/0198314 A1 | 8/2009 | Foster et al. |

(56) References Cited

U.S. PATENT DOCUMENTS

| | | |
|---|---|---|
| 2009/0204171 A1 | 8/2009 | Ameri |
| 2009/0210022 A1 | 8/2009 | Powers |
| 2009/0270948 A1 | 10/2009 | Nghiem et al. |
| 2009/0270956 A1 | 10/2009 | Vase et al. |
| 2009/0281608 A1 | 11/2009 | Foster |
| 2010/0010602 A1 | 1/2010 | Wedan et al. |
| 2010/0016935 A1 | 1/2010 | Strandberg et al. |
| 2010/0103215 A1 | 4/2010 | Iriguchi |
| 2010/0106215 A1 | 4/2010 | Stubbs et al. |
| 2010/0114277 A1 | 5/2010 | Zhao et al. |
| 2010/0125320 A1 | 5/2010 | Polkinghorne et al. |
| 2010/0137928 A1 | 6/2010 | Duncan et al. |
| 2010/0174348 A1 | 7/2010 | Bulkes et al. |
| 2010/0174349 A1 | 7/2010 | Stevenson et al. |
| 2010/0234929 A1 | 9/2010 | Scheuermann |
| 2010/0249892 A1 | 9/2010 | Bulkes et al. |
| 2010/0292744 A1 | 11/2010 | Hill et al. |
| 2010/0331936 A1 | 12/2010 | Perrey et al. |
| 2011/0060394 A1 | 3/2011 | Poore |
| 2011/0079423 A1 | 4/2011 | Zhao et al. |
| 2011/0087299 A1 | 4/2011 | Ameri |
| 2011/0087302 A1 | 4/2011 | Ameri |
| 2011/0093054 A1 | 4/2011 | Ameri |
| 2011/0160805 A1 | 6/2011 | Erbstoeszer et al. |
| 2011/0160816 A1 | 6/2011 | Stubbs et al. |
| 2011/0160817 A1 | 6/2011 | Foster et al. |
| 2011/0160818 A1 | 6/2011 | Struve |
| 2011/0160828 A1 | 6/2011 | Foster et al. |
| 2011/0160829 A1 | 6/2011 | Foster et al. |
| 2011/0208280 A1 | 8/2011 | Li et al. |
| 2011/0218422 A1 | 9/2011 | Atalar et al. |
| 2011/0238146 A1 | 9/2011 | Wedan et al. |
| 2011/0288403 A1 | 11/2011 | Kondabatni et al. |
| 2012/0016451 A1 | 1/2012 | Struve et al. |
| 2012/0022356 A1 | 1/2012 | Olsen et al. |
| 2012/0035698 A1 | 2/2012 | Johnson et al. |
| 2012/0053662 A1 | 3/2012 | Foster et al. |
| 2012/0109270 A1 | 5/2012 | Foster |
| 2012/0143273 A1 | 6/2012 | Stubbs et al. |
| 2012/0161901 A1 | 6/2012 | Stevenson et al. |
| 2012/0179233 A1 | 7/2012 | Wedan et al. |
| 2012/0253340 A1 | 10/2012 | Stevenson et al. |
| 2012/0271394 A1 | 10/2012 | Foster et al. |
| 2013/0116764 A1 | 5/2013 | Walker et al. |
| 2013/0158641 A1 | 6/2013 | Foster et al. |
| 2013/0190849 A1 | 7/2013 | Perrey et al. |
| 2013/0190850 A1 | 7/2013 | Wedan et al. |
| 2013/0282093 A1 | 10/2013 | Walker et al. |
| 2013/0325093 A1 | 12/2013 | Foster |
| 2014/0067030 A1 | 3/2014 | Walker et al. |
| 2014/0114383 A1 | 4/2014 | Foster et al. |
| 2014/0324139 A1 | 10/2014 | Foster et al. |

FOREIGN PATENT DOCUMENTS

| | | |
|---|---|---|
| CN | 101039619 A | 9/2007 |
| EP | 0897997 B1 | 2/2003 |
| EP | 1594564 A1 | 11/2005 |
| EP | 1852810 B1 | 11/2007 |
| JP | 2004141679 A | 5/2004 |
| JP | 2005501673 A | 1/2005 |
| JP | 2005515852 A | 6/2005 |
| JP | 2005515854 A | 6/2005 |
| WO | WO9606655 A1 | 3/1996 |
| WO | WO03063946 A2 | 8/2003 |
| WO | WO03063953 A2 | 8/2003 |
| WO | WO03089045 A2 | 10/2003 |
| WO | WO2004073791 A1 | 9/2004 |
| WO | WO2005030322 A1 | 4/2005 |
| WO | WO2006105066 A2 | 3/2006 |
| WO | WO2006093685 A1 | 9/2006 |
| WO | WO2007047966 A2 | 4/2007 |
| WO | WO2007089986 A1 | 8/2007 |
| WO | WO2007118194 A2 | 10/2007 |
| WO | WO2008051122 A1 | 5/2008 |
| WO | WO2009137186 A1 | 11/2009 |
| WO | WO2010078552 A1 | 7/2010 |

OTHER PUBLICATIONS

"High Voltage Engineering and Testing, 2nd Edition", edited by Hugh M. Ryan, Institution of Engineering and Technology, 2001, 15 pages.
Avalanche Breakdown, Wikipedia Article, captured Apr. 6, 2010, [http://en.wikipedia.org/wiki/Avalanche_breakdown].
Basso, Christophe, "SPICE Model Simulates Spark-Gap Arrestor", Electronics Design, Strategy, and News (EDN), Jul. 3, 1997, 4 pages.
Citel Inc., Data Sheet, BH Series 2 Electrode Miniature Gas Discharge Tube Surge Arrester—8mm, May 14, 2009, 2 pages.
File History for U.S. Appl. No. 11/015,807, filed Dec. 17, 2004.
Gray, Robert W. et al., "Simple design changes to wires to substantially reduce MRI-induced heating at 1.5 T: implications for implanted leads", Magnetic Resonance Imaging 23 (2005) 887-891.
Hayes, David L., Chapter 4, "Generator and Lead Selection" from book entitled "Cardiac Pacing and Defibrillation A Clinical Approach", John Wiley & Sons, (c) 2000 Mayo Foundation, p. 129-157.
International Search Report and Written Opinion issued in PCT/US2008/085518 on Oct. 29, 2009, 15 pages.
International Search Report and Written Opinion issued in PCT/US2009/032838, mailed May 4, 2009, 14 pages.
International Search Report and Written Opinion issued in PCT/US2009/038629, mailed Jun. 29, 2009, 11 pages.
International Search Report and Written Opinion issued in PCT/US2009/056843, mailed Dec. 29, 2009, 13 pages.
International Search Report and Written Opinion issued in PCT/US2010/024062, mailed Sep. 27, 2010.
International Search Report and Written Opinion issued in PCT/US2010/033686 on Aug. 10, 2010, 12 pages.
International Search Report and Written Opinion issued in PCT/US2010/048620, mailed Apr. 5, 2011, 10 pages.
International Search Report and Written Opinion issued in PCT/US2010/053223, mailed Dec. 27, 2010, 11 pages.
International Search Report and Written Opinion issued in PCT/US2010/055130, mailed Mar. 10, 2011, 11 pages.
International Search Report and Written Opinion issued in PCT/US2010/055653, mailed Feb. 1, 2011, 14 pages.
International Search Report and Written Opinion issued in PCT/US2011/052541, dated Mar. 9, 2012, 22 pages.
International Search Report and Written Opinion issued in PCT/US2012/055673, mailed Dec. 13, 2012, 10 pages.
International Search Report and Written Opinion issued in PCT/US2013/037432, mailed Nov. 19, 2013, 17 pages.
International Search Report and Written Opinion issued in PCT/US2013/057732, mailed Dec. 13, 2013, 11 pages.
Invitation to Pay Additional Fees and Partial Search Report, dated Aug. 17, 2009, issued in PCT/US2008/085533, 6 pages.
Invitation to Pay Additional Fees and Partial Search Report, issued in PCT/US2010/024062, mailed May 7, 2010.
Partial International Search Report issued in PCT/US2011/052541, mailed Dec. 6, 2011, 4 pages.
Partial International Search Report issued in PCT/US2013/013432, mailed Jul. 17, 2013, 6 pages.
Partial International Search Report issued in PCT/US2013/037432, mailed Jul. 17, 2013, 6 pages.
Static Spark Gap Analysis, captured Dec. 24, 2002, [http://www.richieburnett.co.uk/static.html].
International Search Report and Written Opinion issued in PCT/US2013/065517, mailed Dec. 20, 2013, 11 pgs.

* cited by examiner

MRI CONDITIONALLY SAFE LEAD WITH LOW-PROFILE CONDUCTOR FOR LONGITUDINAL EXPANSION

CROSS-REFERENCE TO RELATED APPLICATIONS

This application is a continuation of U.S. application Ser. No. 13/767,445, filed Feb. 14, 2013, is now U.S. Pat. No. 8,676,351 which is a continuation of U.S. application Ser. No. 12/940,489, filed Nov. 5, 2010, is now U.S. Pat. No. 8,391, 994 and claims the benefit of U.S. Provisional Application 61/291,556, filed Dec. 31, 2009, all of which are herein incorporated by reference in their entirety.

TECHNICAL FIELD

Various embodiments of the present disclosure generally relate to implantable medical devices. More specifically, embodiments of the present disclosure relate to MRI conditionally safe lead conductors.

BACKGROUND

When functioning properly, the human heart maintains its own intrinsic rhythm and is capable of pumping adequate blood throughout the body's circulatory system. However, some individuals have irregular cardiac rhythms, referred to as cardiac arrhythmias, which can result in diminished blood circulation and cardiac output. One manner of treating cardiac arrhythmias includes the use of a pulse generator (PG) such as a pacemaker, an implantable cardioverter defibrillator (ICD), or a cardiac resynchronization (CRT) device. Such devices are typically coupled to a number of conductive leads having one or more electrodes that can be used to deliver pacing therapy and/or electrical shocks to the heart. In atrioventricular (AV) pacing, for example, the leads are usually positioned in a ventricle and atrium of the heart, and are attached via lead terminal pins to a pacemaker or defibrillator which is implanted pectorally or in the abdomen.

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to radio frequency (RF) pulses of electromagnetic energy in a plane perpendicular to the magnetic field. The resultant electromagnetic energy from these pulses can be used to image the body tissue by measuring the relaxation properties of the excited atomic nuclei in the tissue. In some cases, imaging a patient's chest area may be clinically advantageous. In a chest MRI procedure, implanted pulse generators and leads may also be exposed to the applied electromagnetic fields.

SUMMARY

The various embodiments of the present disclosure relate to an implantable electrical lead including a multi-layer coil conductor configured such that the lead exhibits a predetermined axial stiffness or bending stiffness.

In Example 1, an implantable electrical lead includes a lead body and a multi-layer coil conductor extending within the lead body. The multi-layer coil conductor includes a first coil layer and a second coil layer disposed about the first coil layer. The first and second coil layers are configured such that the multi-layer coil conductor has an axial stiffness substantially equal to an axial stiffness of the lead body adjacent to the multi-layer coil conductor.

In Example 2, the implantable electrical lead according to Example 1, wherein each of the first and second coil layers includes a filar having a filar thickness, a coil outside diameter, and a coil pitch, and wherein one or more of the filar thickness, the coil outside diameter, and the coil pitch are such that the axial stiffness of the multi-layer coil conductor is substantially equal to the axial stiffness of the lead body adjacent to the multi-layer coil conductor.

In Example 3, the implantable electrical lead according to either Example 1 or Example 2, wherein a filar material and a coil wind geometry of the first and second coil layers are such that the axial stiffness of the multi-layer coil conductor is substantially equal to the axial stiffness of the lead body adjacent to the multi-layer coil conductor.

In Example 4, the implantable electrical lead according to any of Examples 1-3, wherein the multi-layer coil conductor is mechanically and electrically connected to an electrode.

In Example 5, the implantable electrical lead according to any of Examples 1-4, wherein the multi-layer coil conductor is configured to allow the electrode to move axially relative to a proximal connector when under tensile load.

In Example 6, the implantable electrical lead according to any of Examples 1-5, further comprising a layer of insulating material between the first and second coil layers.

In Example 7, the implantable electrical lead according to any of Examples 1-6, wherein each filar of the first and second coil layers is individually insulated.

In Example 8, an implantable electrical lead includes a lead body having a longitudinal body lumen, an electrode coupled to the flexible body in the distal region, and a multi-layer coil conductor extending within the longitudinal body lumen and coupled to the electrode. The multi-layer coil conductor includes a first coil layer and a second coil layer disposed about the first coil layer. At least one parameter of the first and the second coil layer is configured such that the lead exhibits a predetermined axial stiffness or bending stiffness. The at least one parameter of the first and second coil layers is at least one of a coil filar thickness, a number of filars, a filar material, a coil winding direction, or a coil diameter. The first and second coil layers are configured such that the multi-layer coil conductor has an axial stiffness substantially equal to an axial stiffness of the lead body adjacent to the multi-layer coil conductor.

In Example 9, the implantable electrical lead according to Example 8, further comprising a third coil layer disposed around the second coil layer, wherein at least one parameter of the third coil layer is configured such that the lead exhibits a predetermined axial bending stiffness.

In Example 10, the implantable electrical lead according to either Example 8 or Example 9, wherein each of the first and second coil layers is formed from one or more filars of a silver core drawn filled tube (DFT) wire having an MP35N cladding.

In Example 11, the implantable electrical lead according to any of Examples 8-10, wherein the multi-layer coil conductor is mechanically and electrically connected to a second electrode coupled to the lead body.

In Example 12, the implantable electrical lead according to any of Examples 8-11, wherein the multi-layer coil conductor allows the second electrode to move axially relative to a proximal connector when under tensile load.

In Example 13, the implantable electrical lead according to any of Examples 8-12, wherein each of the filars of the first and second coil layers is individually insulated.

In Example 14, an implantable electrical lead includes a lead body and a multi-layer coil conductor extending within the lead body. The multi-layer coil conductor includes a first coil layer and a second coil layer disposed about the first coil layer. At least one parameter of the first and the second coil layer is configured such that the multi-layer coil conductor has a pre-determined spring constant along at least a portion of its length. The first and second coil layers are configured such that the multi-layer coil conductor has an axial stiffness substantially equal to an axial stiffness of the lead body adjacent to the multi-layer coil conductor.

In Example 15, the implantable electrical lead according to Example 14, wherein the pre-determined spring constant is such that the lead returns to its original length after axial elongation of the multi-layer coil conductor.

In Example 16, the implantable electrical lead according to either Example 14 or Example 15, wherein the multi-layer coil conductor is mechanically and electrically connected to an electrode coupled to the lead body.

In Example 17, the implantable electrical lead according any of Examples 14-16, wherein the multi-layer coil conductor is configured to allow the electrode to move axially relative to a proximal connector when under tensile load.

In Example 18, the implantable electrical lead according to any of Examples 14-17, wherein the multi-layer coil further comprises a third coil layer disposed around the second coil layer, wherein at least one parameter of the third coil layer is configured such that the lead exhibits a predetermined axial bending stiffness.

In Example 19, the implantable electrical lead according to any of Examples 14-18, further comprising a layer of insulating material between the first and second coil layers.

In Example 20, the implantable electrical lead according to any of Examples 14-19, wherein each filar of the first and second coil layers is individually insulated.

Figure 1:
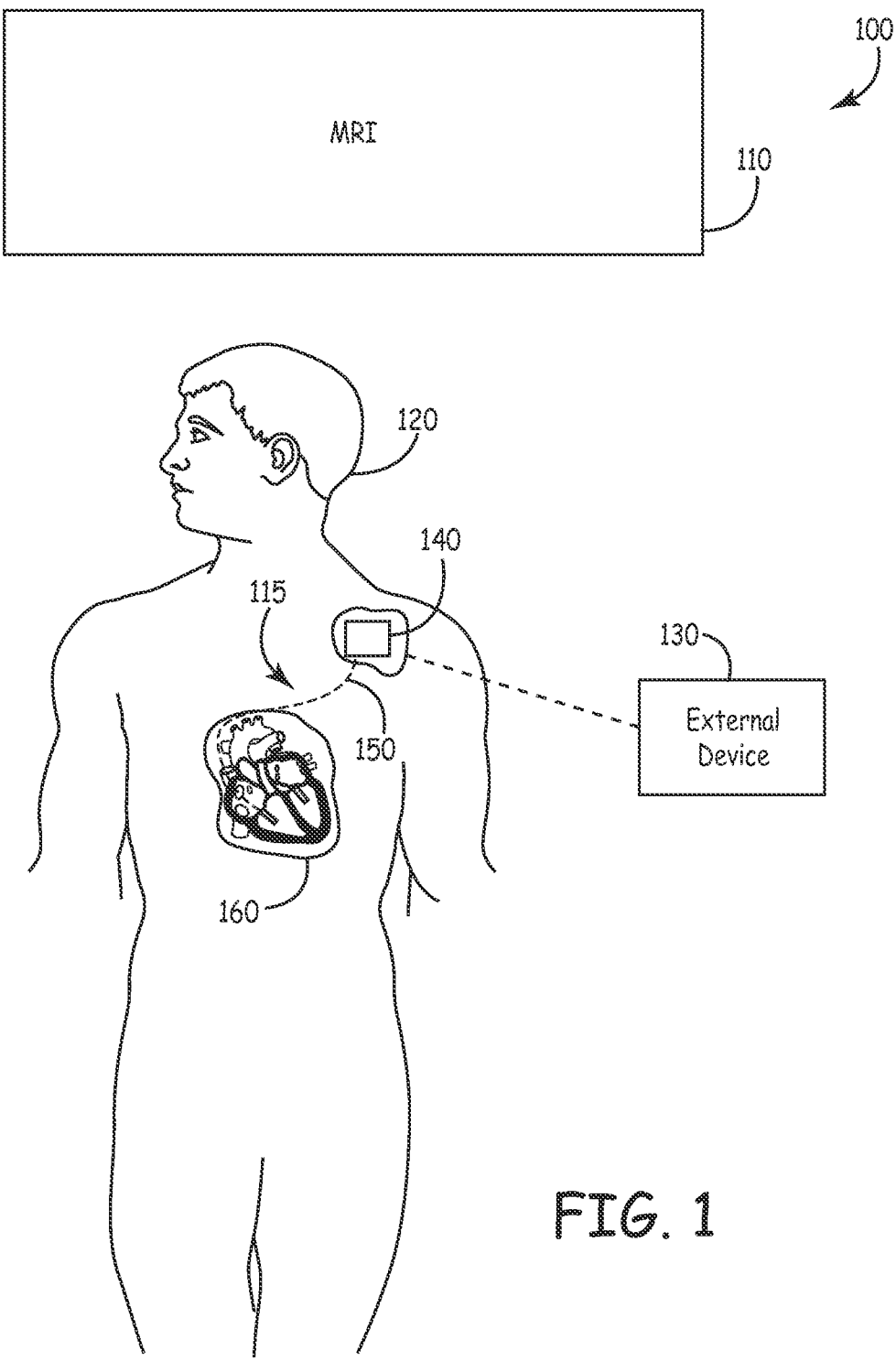
FIG. 1 is a schematic illustration of a medical system including an MRI scanner, and an implantable cardiac rhythm management system implanted within a torso of a human patient according to various embodiments of the present invention.

The drawings have not necessarily been drawn to scale. For example, the dimensions of some of the elements in the figures may be expanded or reduced to help improve the understanding of the embodiments of the present invention. While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

As explained in further detail below, various embodiments of the present invention relate to cardiac rhythm management (CRM) systems incorporating new lead designs advantageously adapted for operation in a magnetic resonance imaging (MRI) environment. In some embodiments, the leads including conductor designs configured to provide suitable electrical performance for delivering pacing and/or defibrillation shock therapy and to minimize the lead's reaction to applied electromagnetic energy during MRI procedures.

In the following description, for the purposes of explanation, numerous specific details are set forth in order to provide a thorough understanding of embodiments of the present invention. It will be apparent, however, to one skilled in the art that embodiments of the present invention may be practiced without some of these specific details.

While, for convenience, some embodiments are described with reference to IMDs in the presence of MRI scanners, embodiments of the present invention may be applicable to various other physiological measurements, treatments, IMD devices, lead types, and other non-invasive examination techniques in which conductive leads are exposed to time varying magnetic fields. As such, the applications discussed herein are not intended to be limiting, but instead exemplary. In addition, various embodiments are applicable to all levels of sensory devices from a single IMD with a sensor to large networks of sensory devices.

FIG. 1 is a schematic illustration of a medical system 100 including an MRI scanner 110, an implantable cardiac rhythm management (CRM) system 115 implanted within a torso of a human patient 120, and one or more external device(s) 130 according to various embodiments. The external device(s) 130 are capable of communicating with the CRM system 115 implanted within the patient 120. In the embodiment shown in FIG. 1, the CRM system 115 includes a pulse generator (PG) 140 and a lead 150. During normal device operation, the PG 140 is configured to deliver electrical therapeutic stimuli to the patient's heart 160 for providing tachycardia ventricular fibrillation, anti-bradycardia pacing, anti-tachycardia pacing, cardiac resynchronization therapy, and/or other types of therapy.

Thus, in the illustrated embodiment, the PG 140 can be an implantable device such as a pacemaker, an ICD, a cardiac resynchronization therapy (CRT) device, a CRT device with defibrillation capabilities (a CRT-D device), or a comparable device. The PG 140 can be implanted subcutaneously within the body, typically at a location such as in the patient's chest. In some embodiments, PG 140 can be implanted in or near the abdomen.

The external device(s) 130 may be a local or remote terminal or other device (e.g., a computing device and/or programming device), operable to communicate with the PG 140 from a location outside of the patient's body. According to various embodiments, external device 130 can be any device external to the patient's body that is telemetry enabled and capable of communicating with the PG 140. Examples of external devices can include, but are not limited to, programmers (PRM), in-home monitoring devices, personal computers with telemetry devices, MRI scanner with a telemetry device, manufacturing test equipment, or wands. In some embodiments, the PG 140 communicates with the remote terminal 130 via a wireless communication interface. Examples of wireless communication interfaces can include, but are not limited to, radio frequency (RF), inductive, and acoustic telemetry interfaces.

Figure 2A:
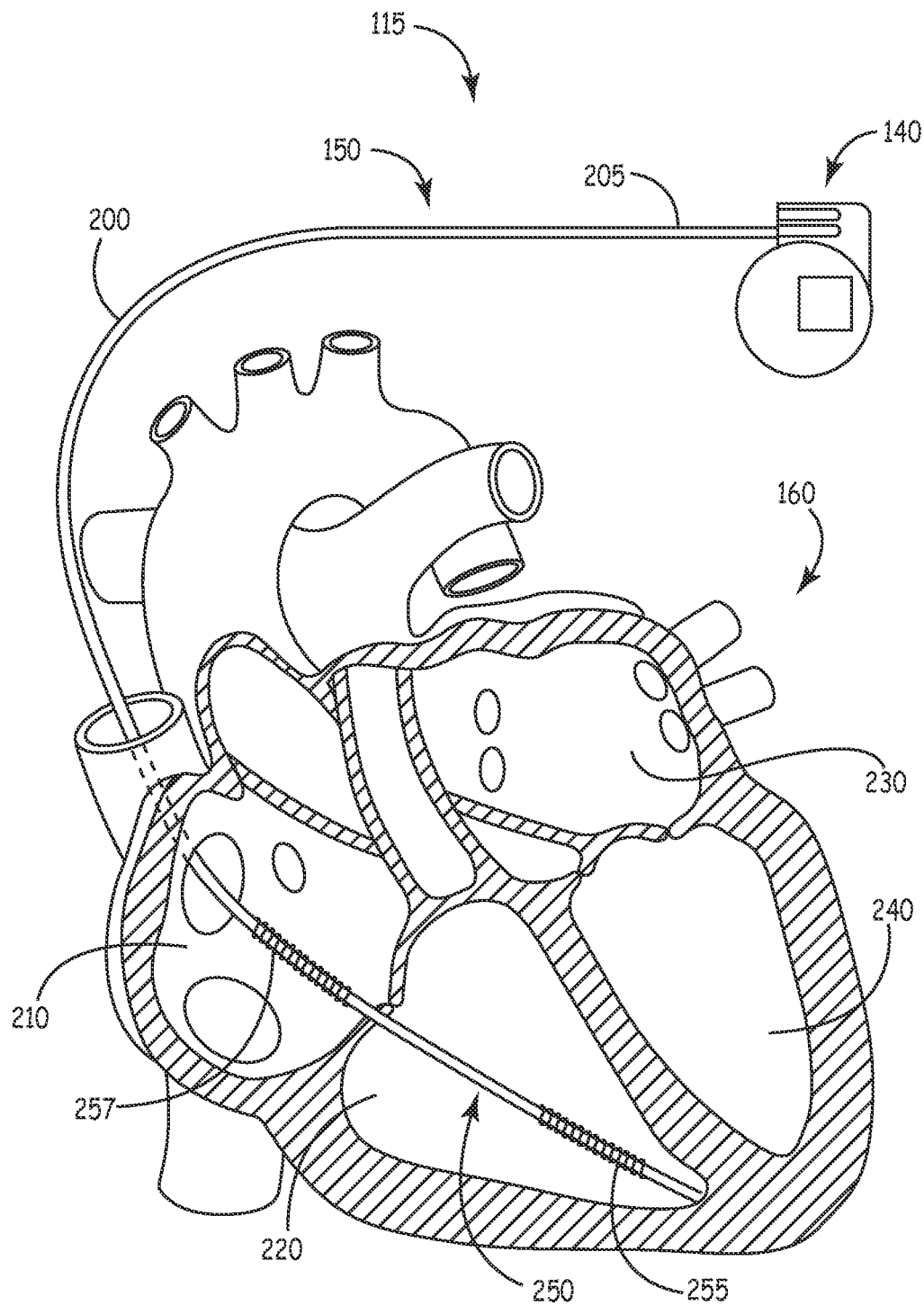
FIG. 2A is a schematic view of an illustrative pulse generator and lead implanted within the body of a patient which may be used in accordance with some embodiments of the present invention.

FIG. 2A is a more detailed schematic view of the CRM system 115 including the illustrative PG 140 equipped with the lead 150 implanted within the body of a patient. In the embodiments depicted, CRM system 115 includes PG 140 implanted near the patient's heart 160 and lead 150 having a distal portion implanted with the patient's heart 160. As can be seen in FIG. 2A, the heart 160 includes a right atrium 210, a right ventricle 220, a left atrium 230, and a left ventricle 240.

The lead 150 has a flexible body 200 including a proximal region 205 and a distal region 250. As shown, the lead 150 is coupled to the PG 140, and the distal region 250 of the lead body 200 is at least partially implanted at a desired location within the right ventricle 220. As further shown, the lead 150 includes a pair of coil electrodes 255, 257 along the distal region 250, such that when implanted as shown in FIG. 2A, they are positioned within the right ventricle 220 and right atrium 210, respectively. As explained and illustrated in further detail below, the lead 150 includes one or more electrical conductors within the lead body 200 (not visible in FIG. 2A) electrically coupling the electrodes 255, 257 to circuitry and other electrical components within the PG 140 for transmitting intrinsic cardiac signals from the heart 160 to the PG 140 and also for transmitting electrical shocks or low-voltage pacing stimuli to the heart 160 via the electrodes 255, 257 or additional electrodes (not shown in FIG. 2A).

Although the illustrative embodiment depicts only a single lead 150 inserted into the patient's heart 160, in other embodiments multiple leads can be utilized so as to electrically stimulate other areas of the heart 160. In some embodiments, for example, the distal portion of a second lead (not shown) may be implanted in the right atrium 210. In addition, another lead may be implanted within the coronary venous system to facilitate pacing the left ventricle, i.e., in a CRT or CRT-D system providing bi-ventricular pacing, as is known in the art. Other types of leads such as epicardial leads may also be utilized in addition to, or in lieu of, the lead 150 depicted in FIGS. 1-2. In short, the various embodiments of the present invention contemplate any multi-lead combinations and configurations for use in CRM systems 115, whether now known or later developed.

During operation, the lead 150 conveys electrical signals between the heart 160 and the PG 140. For example, in those embodiments where the PG 140 has pacing capabilities, the lead 150 can be utilized to deliver electrical therapeutic stimulus for pacing the heart 160. In those embodiments where the PG 140 is an ICD, the lead 150 can be utilized to deliver high voltage electric shocks to the heart 160 via the electrodes 255, 257 in response to an event such as a ventricular fibrillation.

As explained in detail below, various embodiments of the present invention relate to new lead designs that allow for improved mechanical characteristics and safe operation in an MRI environment. In some embodiments, traditional conductor cables are replaced with low profile multi-layer coil conductors. The multi-layer coil conductors allow lead designers to maintain a small lead profile in pace/sense lead applications while better controlling axial elongation of the lead under tensile load.

Figure 2B:
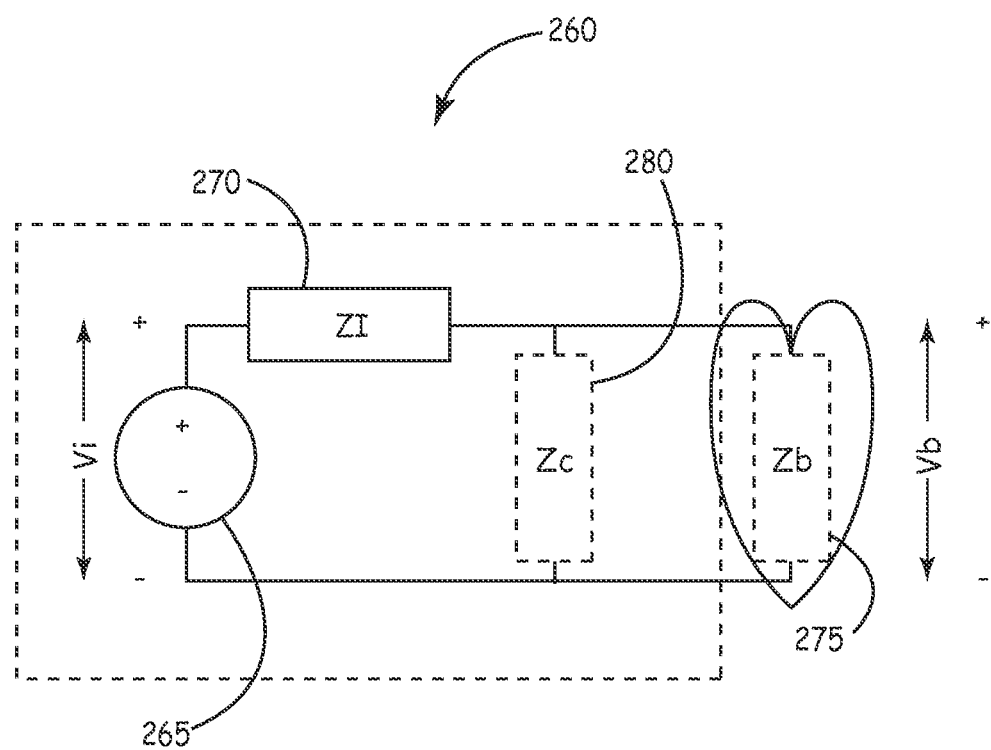
FIG. 2B is a schematic view showing a simplified equivalence circuit for the lead of FIG. 2A

FIG. 2B is a schematic view showing a simplified equivalence circuit 260 for the lead 150 of FIG. 2A, representing the RF energy picked up on the lead 150 from RF electromagnetic energy produced by an MRI scanner. As shown in FIG. 2B, voltage (Vi) 265 in the circuit 260 represents an equivalent source of energy picked up by the lead 150 from the MRI scanner. During magnetic resonance imaging, the length of the lead 150 functions similar to an antenna, receiving the RF energy that is transmitted into the body from the MRI scanner. Voltage (Vi) 265 in FIG. 2B may represent, for example, the resultant voltage received by the lead 150 from the RF energy. The RF energy picked up by the lead 150 may result, for example, from the rotating RF magnetic field produced by an MRI scanner, which generates an electric field in the plane perpendicular to the rotating magnetic field vector in conductive tissues. The tangential components of these electric fields along the length of the lead 150 couple to the lead 150. The voltage (Vi) 265 is thus equal to the integration of the tangential electric field (i.e., the line integral of the electric field) along the length of the lead 150.

The ZI parameter 270 in the circuit 260 represents the equivalent impedance exhibited by the lead 150 at the RF frequency of the MRI scanner. The impedance value ZI 270 may represent, for example, the inductance or the equivalent impedance resulting from the parallel inductance and the coil turn by turn capacitance exhibited by the lead 150 at an RF frequency of 64 MHz for a 1.5 Tesla MRI scanner, or at an RF frequency of 128 MHz for a 3 Tesla MRI scanner. The impedance ZI of the lead 150 is a complex quantity having a real part (i.e., resistance) and an imaginary part (i.e., reactance).

Zb 275 in the circuit 260 may represent the impedance of the body tissue at the point of lead contact. Zc 280, in turn, may represent the capacitive coupling of the lead 150 to surrounding body tissue along the length of the lead 150, which may provide a path for the high frequency current (energy) to leak into the surrounding tissue at the RF frequency of the MRI scanner. Minimizing the absorbed energy (represented by source Vi 265) reduces the energy that is transferred to the body tissue at the point of lead contact with the body tissue.

As can be further seen in FIG. 2B, the lead 150 has some amount of leakage into the surrounding tissue at the RF frequency of the MRI scanner. As further indicated by 275, there is also an impedance at the point of contact of the lead electrodes 255, 257 to the surrounding body tissue within the heart 160. The resulting voltage Vb delivered to the body tissue may be related by the following formula:

$$Vb = Vi\, Zbe/(Zbe+ZI), \text{ where } Zbe = Zb \text{ in parallel with } Zc.$$

The temperature at the tip of the lead 150 where contact is typically made to the surrounding tissue is related in part to the power dissipated at 275 (i.e., at "Zb"), which, in turn, is related to the square of Vb. To minimize temperature rises resulting from the power dissipated at 275, it is thus desirable to minimize Vi (265) and Zc (280) while also maximizing the impedance ZI (270) of the lead 150. In some embodiments, the impedance ZI (270) of the lead 150 can be increased at the RF frequency of the MRI scanner, which aids in reducing the energy dissipated into the surrounding body tissue at the point of contact 275.

In the various embodiments described in further detail below, the impedance of the lead 150 can be increased by adding inductance to the lead 150 and/or by a suitable construction technique. For example, in various embodiments, the inductance of the lead 150 is increased by selectively configuring the conductors used to supply electrical energy to the electrodes 255, 257.

Figure 3:
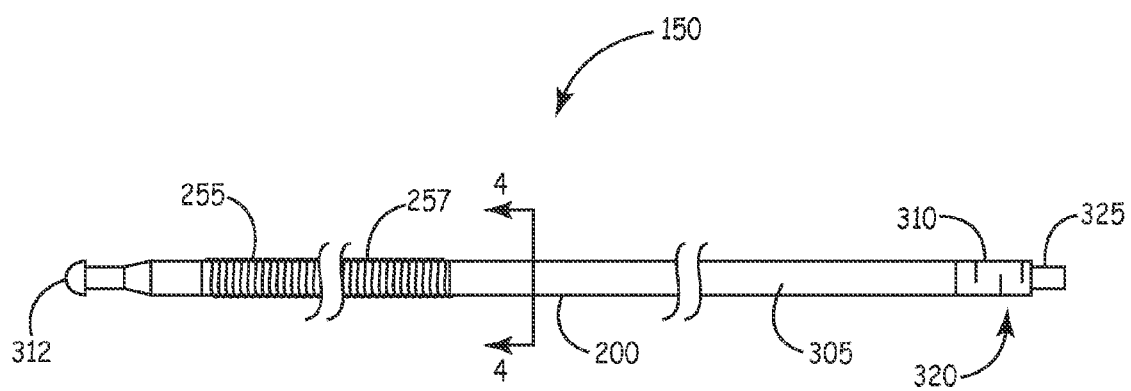
FIG. 3 is a schematic view illustrating an exemplary lead that may be used in accordance with one or more embodiments of the present invention.

FIG. 3 illustrates in further detail the exemplary lead 150 that may be used in accordance with one or more embodiments of the present invention. As shown in FIG. 3, the lead body 200 includes a proximal end 305, and the lead 150 further includes a connector assembly 310 coupled to the proximal end 305 of the lead body, the coil electrodes 255, 257, and a tip electrode 312 which operates in the illustrated embodiment as a pace/sense electrode. Depending on the functional requirements of the PG 140 (see FIG. 1), and the therapeutic needs of the patient, the distal region 250 of the lead 150 may include additional electrodes. For example, in some embodiments, the pair of coil electrodes 255, 257 can be used to function as shocking electrodes for providing a defibrillation shock to the heart 160. In some embodiments, the lead 150 can include a low-voltage (e.g., ring) electrode proximal to the distal tip of the lead 150 which is also operable as a pace/sense electrode, which can be included in addition to, or in lieu of, the tip electrode 312. In short, the lead 150 can incorporate any number of electrode configurations within the scope of the embodiments of the present invention.

In the illustrated embodiment, the connector assembly 310 includes a connector body 320 and a terminal pin 325. The connector assembly 310 is coupled to the lead body 200 and can be configured to mechanically and electrically couple the lead to a header on PG 140 (see FIG. 1 and FIG. 2). In various embodiments, the terminal pin 325 extends proximally from the connector body 320 and in some embodiments is coupled to an inner conductor (not shown in FIG. 3) that extends longitudinally through the lead body 200 to the tip electrode 312. In some embodiments, the terminal pin 325 can include an aperture extending therethrough communicating with a lumen defined by the inner conductor coil in order to accommodate a guide wire or an insertion stylet.

In various embodiments, the tip electrode 312 is in the form of an electrically active fixation helix at the distal end of the lead 150. In some embodiments, the tip electrode 312 can be an extendable/retractable helix supported by a mechanism to facilitate longitudinal translation of the helix relative to the lead body as the helix is rotated. In those embodiments, the terminal pin 325 may be rotatable relative to the connector body 320 and the lead body 200 such that rotation of the terminal pin 325 relative to the lead body 200 causes the inner conductor, and in turn, the helical tip electrode to rotate and translate longitudinally relative to the lead body 200. Various mechanisms and techniques for providing extendable/retractable fixation helix assemblies (both electrically active and passive) are known to those of ordinary skill in the art, and need not be described in greater detail here.

The pace/sense electrode (whether a solid tip electrode as described above or an active-fixation helix such as shown in FIG. 3) can be made of any suitable electrically conductive material such as Elgiloy, MP35N, tungsten, tantalum, iridium, platinum, titanium, palladium, stainless steel, as well as alloys of any of these materials.

The coil electrodes 255, 257 can take on any configuration suitable for delivering a relatively high-voltage therapeutic shock to the heart for defibrillation therapy. In various embodiments, the coil electrodes 255, 257 can be made from any suitable electrically conductive material such as those discussed in the preceding paragraph. The lead 150 also includes a conductor (not shown in FIG. 3) within the lead body 200 electrically connecting the coil electrodes 255, 257 to an electrical contact on the connector assembly 310, which in turn is configured to electrically couple the coil electrodes 255, 257 to electrical components within the PG 140.

Figure 4:
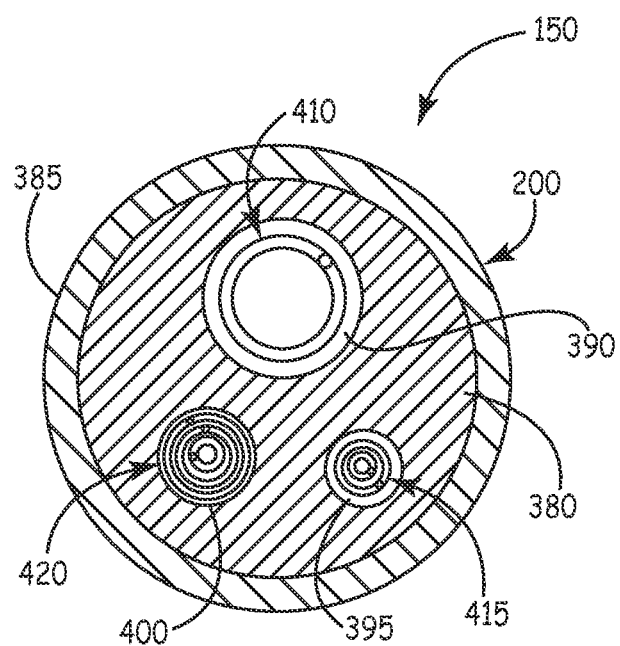
FIG. 4 is a transverse cross-sectional view of the lead of FIG. 3 taken along the line 4-4 in FIG. 3.

In FIG. 4 is a transverse cross-sectional view of the lead 150 taken along the line 4-4 in FIG. 3. As shown in FIG. 4, the lead body 200 includes an inner tubular member 380 and an outer tubular member 385 disposed over and bonded to the inner tubular member 380. The tubular members 380, 385 can be made from any number of flexible, biocompatible insulative materials, including without limitation, polymers such as silicone and polyurethane, and copolymers thereof. As further shown, the inner tubular member 380 includes a plurality of lumens 390, 395, 400, and conductors 410, 415, and 420 are disposed, respectively, in the lumens 390, 395, and 400. Each of the conductors 410, 415 and 420 extends longitudinally within the respective lumen 390, 395, 400, and is electrically coupled to an electrode (e.g., the electrodes 312, 255, or 257 in FIG. 3) and also to an electrical contact of the connector assembly 310.

In some embodiments, the lead body 200 does not include separate, coaxial tubular members, but instead, includes only a single tubular member (e.g., the member 380) including one or more longitudinal lumens for housing the requisite conductors. For illustrative purposes, the three lumens 390, 395, 400 of the inner tubular member 380 are shown having different diameters. In other embodiments, however, the relative dimensions and/or locations of the lumens 390, 395, 400 may vary from that shown. In addition, the inner tubular member 380 may include a greater or lesser number of lumens, depending on the particular configuration of the lead 150. For example, the inner tubular member 380 may include a greater number of lumens to house additional conductor wires and/or electrode coils within the lead 150 for supplying current to other shocking coils and/or pace/sense electrodes.

In the illustrated embodiment, the conductor 410 is a single layer coil conductor such as would be used in conjunction with a conventional, low-voltage pace/sense electrode, e.g., the tip electrode 312. In some embodiments, for example, the coil conductor 410 is configured to have a relatively high impedance when exposed to electromagnetic energy such as that present during an MRI scan. In various such embodiments, the coil conductor 410 is configured according to the various embodiments described, for example, in U.S. Patent Application Publication No. 2009/0198314, which is incorporated herein by reference in its entirety. The increased impedance aids in reducing the energy dissipated into the surrounding body tissue at or near the lead electrode(s). In various embodiments, the conductor 410 and the lumen 390 are omitted.

As explained in further detail below, the conductors 415 and 420 are multi-layer conductor assemblies incorporated into the lead 150 to provide a conditionally-safe MRI-compatible lead design, as well as to provide improved fatigue resistance and other mechanical properties during delivery and under chronic operating conditions. In various embodiments, the multi-layer coil conductors 415, 420 include multiple coil layers having selectively controlled coil properties (e.g., pitch, outside diameter, filar thickness, etc.) to make a highly inductive, highly conductive, small diameter conductor that has suitable mechanical characteristics for a stimulation/sensing lead body.

In the illustrated embodiment, the coil conductor 415 is a three-layer conductor and the coil conductor 420 is a two-layer conductor. In various embodiments, multi-layer coil conductors utilizing more than three coil layers can be utilized. In various embodiments, the single layer coil conductor 410 can be replaced with a multi-layer coil conductor similar or identical to the coil conductor 415 and/or 420.

Figure 5:
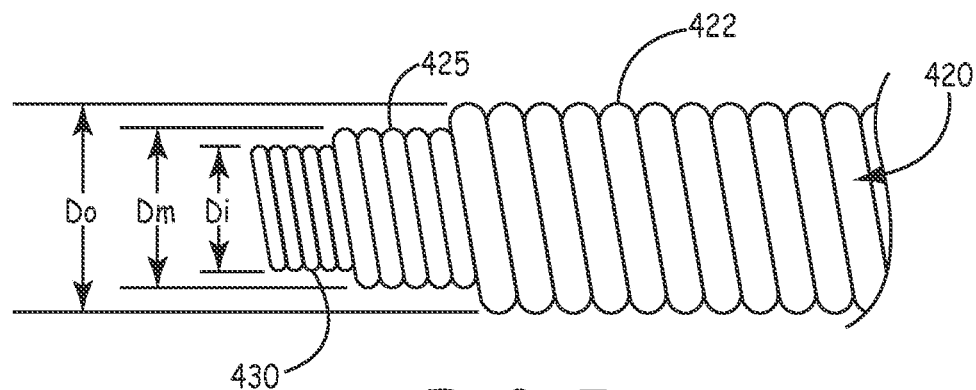
FIG. 5 illustrates invention detail of a multi-layer coil conductor utilized in the lead of FIG. 3 according to an embodiment of the present invention.

FIG. 5 is a more detailed side view of the coil conductor 420 according to one embodiment of the present invention. As shown in FIG. 5, the multi-layer coil conductor 420 is a three-layer coil conductor 420 including an outer coil layer 422, a middle coil layer 425 and an inner coil layer 430. The outer coil layer 422 is disposed about the middle coil layer 425 which is disposed about the inner coil layer 430. The outer, middle, and inner coil layers 422, 425, 430 are electrically coupled to one another in parallel at least at their the proximal ends (i.e., at or near the connector assembly) as well as at their distal ends (i.e., at the electrode 255), so as to provide parallel conductive paths between the connector assembly 310 and the electrode 255. In various embodiments, the parameters of the coil layers 422, 425 and 430 are configured such that the multi-layer coil conductor 420 has a maximum DC resistance of about 3.0-3.5 ohms, and a high impedance when exposed to an external alternating magnetic field characterized by frequencies associated with MRI scans. It will be appreciated that the two-layer coil conductor 415 can be configured in substantially the same manner as the coil conductor 420 shown in FIG. 5 while only including two coil conductor layers.

In some embodiments, the outer layer 422 of the coil conductor 420 can be wound to coil diameter $D_o$ of less than about 0.013 inches. In some embodiments, the outer layer is close pitched and can have one or more filars having a maximum filar thickness of about 0.004 inches. In accordance with various embodiments, the outer layer may or may not be present depending on the desired application of the lead. For example, in some cases, the outer layer may be used to change the resistance of the multi-layer coil conductor 420. In at least one embodiment, the outer layer 422 may have a filar thickness of from about 0.001 to about 0.004 inches.

The middle layer 425 of the coil conductor 420 is close pitched and can be wound to a coil diameter $D_m$ less than the inner diameter of the outer coil layer 422. In some embodiments, the middle layer can have one or more filars having a maximum filar thickness of from about 0.0007 to about 0.003 inches.

The inner coil layer 430 of the coil conductor 420 is close pitched and can be wound to a coil diameter $D_i$ less than the inner diameter of the middle layer 425. In some embodiments, the inner layer can have one or more filars having a maximum filar thickness of from about 0.0007 to about 0.001 inches.

Of course, in various other embodiments, multi-layer coil conductor 420 utilizes different ranges of dimensions and other parameters (e.g., filar count) of the respective coil layers 422, 425, 430 depending on the operational needs for the lead 150.

In the various embodiments, the filar material can be any suitable material exhibiting the desired electrical and mechanical properties. In one embodiment, the filars of the outer, middle, and/or inner coil layers 422, 425, 430 are made of drawn filled tube (DFT) wire including a silver core (about 40%) with an MP35N or tantalum cladding. In another embodiment, the outer, middle, and/or inner coil layers 422, 425, 430 are made of DFT wire including a tantalum core with a MP35N cladding. The coil layers 422, 425, 430 may be comprised of the same or different materials, and each of the coil layers 422, 425, 430 may include different silver fill levels.

In various embodiments, the filars of each layer of the coil conductor 420 are wound in the same pitch direction. That is, the individual filars of each coil layer are wound to have either a right-hand pitch or a left-hand pitch when viewing the coil along its longitudinal axis.

In various embodiments, one or more of the coil layers 422, 425, 430 has a variable coil pitch along its length, which operates to de-tune the coil conductor 420 to reduce the effect of externally applied electromagnetic radiation (i.e., due to an MRI chest scan).

In various embodiments, the individual coil layers 422, 425 and 430 can be separately optimized to each exhibit a different inductance, e.g., by modifying the filar thickness, pitch, and/or coil layer diameter, to further modify the performance of the lead 150 under MRI conditions.

Some embodiments of the present invention include one or more layers of insulation between one or more of the adjacent coil layers 422, 425 or 430. Alternatively, or additionally, in various embodiments, the individual filars or the coil layers 422, 425, and/or 430 are individually insulated. Any suitable insulation material can be utilized, if desired. Exemplary insulating materials for the filars and/or between the coil layers include ethylene tetrafluoroethylene (ETFE), polytetrafluoroethylene (PTFE), expanded PTFE (ePTFE), silicone, and the copolymers of the foregoing.

The various embodiments of the lead 150 described above, advantageously minimize induced currents in the lead conductors resulting from exposure to external MRI electromagnetic fields. This is in contrast to conventional lead systems utilizing stranded cable conductors to transmit the shocking currents from the PG to the shocking electrodes. While such cable conductors provide excellent electrical performance for delivering anti-tachycardia therapy, stranded cable conductors also have a low impedance and thus are susceptible to generation of induced currents when exposed to an alternating electromagnetic field such as that present during an MRI scan. Various embodiments of the present invention can result in lead 150 exhibiting a temperature rise when exposed to MRI radiation of approximately half that experienced utilizing traditional high energy cables which are conventionally utilized to supply energy to high-voltage shocking coils in defibrillation leads. The high impedance conductor configurations for the lead 150 described above minimize the effects of MRI radiation while still providing suitable electrical performance for use in anti-tachycardia therapy applications.

In addition, In accordance with some embodiments, the design parameters of the multi-layer coil conductors can be tuned to control the mechanical properties, e.g., effective spring constant and thus stiffness of the overall lead assembly, bending stiffness, and the like. Such tuning may enable the user minimize stresses (loads) on adjacent (distal) polymer components, minimize the potential for shear bond failure, facilitate/control the lead bias shape, and minimize the impact of axial length tolerance stack-up during assembly, in both low and high voltage lead applications. For example, in various embodiments, the shocking coils 255, 257 (see FIGS. 2A and 3) are omitted, and the lead 150 includes only one or more low-voltage pace/sense electrodes such as the tip electrode 312 and additional ring electrodes along the lead 150. In such embodiments, multi-layer coil conductors such as the coil conductors 425 and/or 420 can be utilized to provide sufficient electrical performance in a low-profile design and also optimal mechanical characteristics such as axial stiffness relative to that of adjacent insulative components such as the lead body 200.

In various embodiments, the multi-layer coil conductor 415 and/or 420 can be tuned to control the effective spring constant (expressed in force per unit length) of the coil conductor 415 and/or 420 so as to reduce or eliminate the difference in axial stiffness between the conductor coil and the adjacent insulating elements (i.e., lead body 200 components). By controlling and optimizing the coil conductor spring constant/axial stiffness in this way, the overall axial strength of the polymeric lead body components can be maintained, for example, where the coil conductor 415, 420 terminates proximal to the lead body component. Additionally, by reducing or eliminating large differences in the axial stiffness of the conductors (i.e., by utilizing the multi-layer coil conductors 415 and/or 420) and the parallel polymeric lead body components, shear forces between these elements are advantageously reduced. Utilizing the multi-layer coil conductors 415, 420 in lieu of conductor cables also eliminates snaking of the conductor that can result due to the contraction and release of a tensile axial load on the conductor.

Exemplary design parameters that can be varied to tune/optimize the mechanical characteristics discussed above can include, without limitation, the selection of conductor materials, number of layers, wind geometry, pitch, filar diameter, number of filars, and others.

In addition to the coil conductor configurations described above, the various embodiments of the lead 150 of the present invention may optionally incorporate other features or techniques to minimize the effects of MRI radiation. For example, in some embodiments, shielding may be added to the lead 150 to further reduce the amount of electromagnetic energy picked up from the lead 150. For example, the energy picked up from the shielding can be coupled to the patient's body along the length of the lead 150, preventing the energy from coupling to the lead tip. The transfer of intercepted energy by the shielding along the length of the shielding/lead can also be inhibited by dissipating the energy as resistive loss, using resistive material for the shielding construction.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An implantable electrical lead comprising:
   a lead body; and
   a coil conductor extending within the lead body, the coil conductor configured such that the coil conductor has an axial stiffness substantially equal to an axial stiffness of the lead body adjacent to the coil conductor.

2. The implantable electrical lead of claim 1, wherein the coil conductor includes a filar having a filar thickness, a coil outside diameter, and a coil pitch, and wherein one or more of the filar thickness, the coil outside diameter, and the coil pitch are such that the axial stiffness of coil conductor is substantially equal to the axial stiffness of the lead body adjacent to the coil conductor.

3. The implantable electrical lead of claim 1, wherein a filar material and a coil wind geometry of the coil conductor are such that the axial stiffness of the coil conductor is substantially equal to the axial stiffness of the lead body adjacent to the coil conductor.

4. The implantable electrical lead of claim 1, wherein the coil conductor is mechanically and electrically connected to an electrode.

5. The implantable electrical lead of claim 4, wherein the coil conductor is configured to allow the electrode to move axially relative to a proximal connector when under tensile load.

6. The implantable electrical lead of claim 1, further comprising a layer of insulating material disposed over the coil conductor.

7. The implantable electrical lead of claim 1, wherein each filar of the coil conductor is individually insulated.

8. The implantable electrical lead of claim 1, wherein the coil conductor is formed from one or more filars of a silver core drawn filled tube (DFT) wire having an MP35N cladding.

9. The implantable electrical lead of claim 1, wherein a pre-determined spring constant of the coil conductor is such that the lead returns to its original length after axial elongation of the coil conductor.

10. An implantable electrical lead, comprising:
    a lead body having a longitudinal body lumen;
    an electrode coupled to the flexible body in the distal region; and
    a conductor extending within the longitudinal body lumen and coupled to the electrode, wherein at least one parameter of the coil conductor is configured such that the lead exhibits a predetermined axial stiffness or bending stiffness, wherein the at least one parameter of the coil conductor is at least one of a coil filar thickness, a number of filars, a filar material, a coil winding direction, or a coil diameter, and wherein the coil conductor is configured such that the coil conductor has an axial stiffness substantially equal to an axial stiffness of the lead body adjacent to the coil conductor.

11. The implantable electrical lead of claim 10, wherein the coil conductor is formed from one or more filars of a silver core drawn filled tube (DFT) wire having an MP35N cladding.

12. The implantable electrical lead of claim 10, wherein the coil conductor is mechanically and electrically connected to a second electrode coupled to the lead body.

13. The implantable electrical lead of claim 12, wherein the coil conductor allows the second electrode to move axially relative to a proximal connector when under tensile load.

14. The implantable electrical lead of claim 10, wherein each of the filars of the coil conductor is individually insulated.

15. An implantable electrical lead, comprising:
    a lead body; and
    a coil conductor extending within the lead body, wherein at least one parameter of the coil conductor is configured such that the coil conductor has a pre-determined spring constant along at least a portion of its length, and wherein the coil conductor is configured such that the coil conductor has an axial stiffness substantially equal to an axial stiffness of the lead body adjacent to the coil conductor.

16. The implantable electrical lead of claim 15, wherein the pre-determined spring constant is such that the lead returns to its original length after axial elongation of the coil conductor.

17. The implantable electrical lead of claim 15, wherein the coil conductor is mechanically and electrically connected to an electrode coupled to the lead body.

18. The implantable electrical lead of claim 15, wherein the coil conductor is configured to allow the electrode to move axially relative to a proximal connector when under tensile load.

19. The implantable electrical lead of claim 15, further comprising a layer of insulating material disposed over the coil conductor.

20. The implantable electrical lead of claim 15, wherein each filar of the coil conductor is individually insulated.

* * * * *